United States Patent
Kobayashi et al.

[11] Patent Number: 5,817,487
[45] Date of Patent: Oct. 6, 1998

[54] HEPARAN SULFATE 2-O-SULFOTRANSFERASE

[75] Inventors: Masashi Kobayashi; Hiroko Habuchi; Osami Habuchi; Koji Kimata, all of Aichi-ken, Japan

[73] Assignee: Seikagaku Kogyo Kabushiki Kaisha, Tokyo, Japan

[21] Appl. No.: 685,659

[22] Filed: Jul. 24, 1996

[30] Foreign Application Priority Data

Jul. 24, 1995 [JP] Japan .................................. 7-187577

[51] Int. Cl.⁶ ............................ C12P 19/00; C12P 19/26; C12P 11/00; C12N 9/10
[52] U.S. Cl. .............................. 435/84; 435/72; 435/130; 435/193; 435/358; 536/21
[58] Field of Search ..................... 435/193, 358, 435/84, 130, 72; 536/21

[56] References Cited

FOREIGN PATENT DOCUMENTS 96305410  1/1996  European Pat. Off. .

OTHER PUBLICATIONS

Bame et al., Biosynthesis of Heparan Sulfate. Coordination of Polymer–Modification Reactions in a Chinese Hamster Ovary Cell Mutant Defective in N–Sulfotransferase, J. Biol. Chem., 266:10287–10293, 1991.

Habuchi et al., Secretion of Chondroitin 6–Sulfotransferase and Chondroitin 4–Sulfotransferase from Cultured Chick Embryo Chondrocytes, Biochim. Biophys. Acta 1133:9–16, 1991.

Hollmann et al., Purification and Characterization of a 3'–Phosphoadenylylsulfate:Chondroitin 6–Sulfotransferase from Arterial Tissue, Biol. Chem. Hoppe–Seyler, 367:5–13, 1986.

ATCC Catalogue of Cell Lines and Hybridomas, Sixth Edition, p. 360, 1988.

The Journal of Biological Chemistry, vol. 269, No. 40, Oct. 7, 1994 pp. 24538–24541, Wald, H. et al.: "Biosynthesis of Heparin".

Glycoconjugate Journal, vol. 8, No. 3, Jun./1991, pp. 200–201, Wald, H. et al.: "Partial Purification of O–Sulfotransferases involved in the Biosynthesis of Heparin".

The Journal of Biological Chemistry, vol. 264, No. 14, May 15, 1989, pp. 8059–8065, Bame, K. and Esko, J.: "Undersulfated Heparan Sulfate in a Chinese Hamster Ovary N–Sulfotransferase".

The Journal of Biological Chemistry, vol. 271, No. 13, Mar. 29, 1996, pp. 7645–7653, Kobayashi M. et al.: "Purification and Characterization of heparan Sulfate 2–Sulfotransferase from Cultured Chinese Hamster Ovary Cells".

*Primary Examiner*—David M. Naff
*Assistant Examiner*—Janet M. Kerr
*Attorney, Agent, or Firm*—Knobbe, Martens, Olson & Bear, LLP

[57] ABSTRACT

Heparan sulfate 2-O-sulfotransferase having the following properties is obtained from, for example, CHO cells:

(i) action: sulfate group is transferred from a sulfate group donor selectively to the hydroxyl group at C-2 position of iduronic acid residue of a sulfate group acceptor;

(ii) substrate specificity: sulfate group is transferred to heparan sulfate or CDSNS-heparin, but sulfate group is not transferred to chondroitin, chondroitin sulfate, dermatan sulfate, and keratan sulfate;

(iii) optimum reaction pH: about pH 5 to 6.5;

(iv) optimum ionic strength: about 50 to 200 mM when sodium chloride is used; and (v) inhibition and activation: the activity of the enzyme is increased by protamine, the activity of the enzyme is inhibited by adenosine-3',5'-diphosphate, and the activity of the enzyme is scarcely affected by dithiothreitol at 10 mM or less.

9 Claims, 9 Drawing Sheets

HEPARAN SULFATE 2-O-SULFOTRANSFERASE

TECHNICAL FIELD

The present invention relates to a novel sulfotransferase. In particular, the present invention relates to a heparan sulfate 2-O-sulfotransferase which selectively transfers sulfate group to the hydroxyl group at C-2 position of iduronic acid residue contained in heparin and heparan sulfate.

BACKGROUND OF THE INVENTION

Heparin and heparan sulfate are polysaccharide belonging to glycosaminoglycan. Heparin and heparan sulfate have similar fundamental sugar chain structure, both are produced by synthesis of a chain composed of N-acetylglucosamine (GlcNAc) and glucuronic acid (GlcA) linked by 1→4 bond, followed by processing, however, the degree of processing is different between the both. Namely, although the both are charged strongly negatively, heparin contains larger amounts of N-sulfated glucosamine, 6-O-sulfated glucosamine, and 2-O-sulfated iduronic acid. Heparan sulfate and heparin are present in tissues in a form of proteoglycan in which the sugar chain covalently binds to a core protein, in the same manner as other glycosaminoglycans.

Heparin proteoglycan has been found in secretory granules of mast cells and basophilic cells, and considered to participate in packaging of histamine and basic protease. Heparan sulfate proteoglycan is widely distributed, for example, over extracellular matrices and cell surfaces, and has been known to have various functions such as those relevant to differentiation, growth and movement of cells, and anticoagulation.

By the way, basic fibroblast growth factor (bFGF) is a protein which strongly facilitates growth of an extremely wide variety of cells such as those of vascular system, connective tissue system, brain nervous system, and immune system. On the other hand, acidic fibroblast growth factor (aFGF) is a protein which is often found in nervous system such as brain and retina. Since aFGF binds to a cell surface receptor common to bFGF, the both are considered to have essentially the same acting mechanism.

It has been revealed that aFGF and bFGF strongly bind to a sugar chain moiety of heparan sulfate proteoglycan incorporated in extracellular matrices or basement membranes of tissues. Recently, it has been suggested that a heparin or heparan sulfate chain is essential for bFGF to bind to a high affinity receptor (Yayon, A. et al., *Cell*, 64, 841–848 (1991)); Rapraeger, A. C., *Science*, 252, 1705–1708 (1991)). Further, it has been suggested that the bFGF activity also requires binding of these sugar chains to the high affinity receptor itself (Kan, M. et al., *Science*, 259, 1918–1921 (1993); Guimond, S. et al., *J. Biol. Chem.*, 268 23906–23914 (1993)). The present inventors have demonstrated that a particular structural domain concerning binding to bFGF is present on the chain of heparan sulfate, and that the binding of bFGF to the chain of heparan sulfate greatly affects metabolism of bFGF (Habuchi, H. et al. (1992) *Biochem. J.*, 285, 805–813). It is known that binding of bFGF requires the presence of 2-O-sulfate group of iduronic acid residue and N-sulfated glucosamine residue in the heparan sulfate chain (Habuchi, H. et al., *Biochem. J.*, 285, 805–813 (1992); Turnbull, J. E. et al., *J. Biol. Chem.*, 267, 10337–10341 (1992)).

It has been reported that heparan sulfate relevant to formation of highly organized basement membrane has a high degree of sulfation at C-6 position of glucosamine residue (Nakanishi, H. et al., *Biochem. J.*, 288, 215–224 (1992)). It has been also reported that the affinity of heparin to fibronectin increases in proportion to the molecular weight and the sulfate content of heparin (Ogamo, A. et al., *Biochim. Biophys. Acta*, 841, 30–41 (1985)). It is also known that the higher the ability of metastasis of a cell strain clone originating from Lewis-lung-carcinoma is, the more the content of 6-O-sulfate in synthesized heparan sulfate is (Nakanishi, H., *Biochem. J.*, 288, 215–224 (1992)), and that the degree of sulfation of heparan sulfate decreases in accordance with malignant alteration. Accordingly, it is considered that sulfation plays an important role in expressing physiological activities of heparin and heparan sulfate.

Considering the importance of sulfation in expression of physiological activities of heparin and heparan sulfate, a method for sulfating a specific site of heparin and heparan sulfate may be essential for analysis of physiological activities and modification of functions of heparin and heparan sulfate. A method for chemically introducing sulfate group selectively with regard to N- or O-sulfation has been already reported ("Shin-Seikagaku-Jikken-Koza 3, Toshitsu (Saccharides) II", p324, published by Tokyo-Kagaku-Dojin). However, it requires complicated treatment operations, requires many kinds of reagents, and takes a long time. Thus a method for enzymatically introducing sulfate group has been demanded. A heparan sulfate (GlcN) 2-N-sulfotransferase has been isolated and purified as an enzyme for N-selectively introducing sulfate group into glucosamine (GlcN) residue ("Shin-Seikagaku-Jikken-Koza 3, Toshitsu II", p194, published by Tokyo-Kagaku-Dojin). It has been also attempted to isolate and purify an enzyme which transfers sulfate group selectively to C-2 position of iduronic acid (IdoA) residue of heparin and heparan sulfate (heparan sulfate (IdoA) 2-O-sulfotransferase). However, it was reported that the enzyme was contaminated with heparan sulfate (GlcN) 6-O-sulfotransferase (an enzyme for transferring sulfate group selectively to C-6 position of glucosamine residue of heparin and heparan sulfate; hereinafter simply referred to as "heparan sulfate 6-sulfotransferase", if necessary) even after purification to a high degree, and the separation of the both was difficult (Wald, H. et al., *Glycoconjugate J.*, 8, 200–201 (1991)). Recently, the present inventors have succeeded in isolating and purifying heparan sulfate 6-O-sulfotransferase (*J. Biol. Chem.*, 270, 4712–4719 (1995)). However, heparan sulfate (IdoA) 2-O-sulfotransferase has not been isolated and purified.

Considering the importance of sulfation in expression of physiological activities of heparin and heparan sulfate, it is very important to develop a method for transferring sulfate group to heparin and heparan sulfate not only to study functional analysis of heparin and heparan sulfate but also to provide heparin and heparan sulfate for the purpose of creation of pharmaceuticals having physiological activities preferable for human. Especially, heparan sulfate (GlcN) 2-N-sulfotransferase and heparan sulfate (GlcN) 6-O-sulfotransferase have now been isolated, and thus isolation and purification of heparan sulfate (IdoA) 2-O-sulfotransferase have been desired.

SUMMARY OF THE INVENTION

The present invention has been made taking the aforementioned viewpoints into consideration, an object of which is to provide a heparan sulfate 2-O-sulfotransferase which selectively introduces sulfate group into the hydroxyl group at C-2 position of iduronic acid residue of heparin and heparan sulfate.

The present inventors have diligently searched for an enzyme which selectively transfers sulfate group to the hydroxyl group at C-2 position of iduronic acid residue contained in heparin and heparan sulfate, that is heparan sulfate 2-O-sulfotransferase (hereinafter referred to as "heparan sulfate 2-sulfotransferase" or "the enzyme of the present invention", if necessary), succeeded in isolation and purification of the enzyme, confirmed that the enzyme selectively transfers sulfate group to the hydroxyl group at C-2 position of iduronic acid residue of heparin and heparan sulfate, and achieved the present invention.

Namely, the present invention provides a heparan sulfate 2-O-sulfotransferase having the following properties:

(i) action: sulfate group is transferred from a sulfate group donor selectively to the hydroxyl group at C-2 position of iduronic acid residue of a sulfate group acceptor;

(ii) substrate specificity: sulfate group is transferred to heparan sulfate, heparin, or chemically modified heparin obtained by completely desulfating N,O-sulfate groups of heparin followed by N-resulfation (completely desulfated, N-sulfated heparin; hereinafter reffered to as "CDSNS-heparin"), but sulfate group is not transferred to chondroitin, chondroitin sulfate, dermatan sulfate, and keratan sulfate;

(iii) optimum reaction pH: about 5 to 6.5;

(iv) optimum ionic strength: about 50 to 200 mM when sodium chloride is used; and (v) inhibition and activation: the activity of the enzyme is increased by protamine, the activity of the enzyme is inhibited by adenosine-3',5'-diphosphate (3',5'-ADP), and the activity of the enzyme is scarcely affected by dithiothreitol (DTT) at 10 mM or less.

The present invention also provides a method for producing heparan sulfate 2-O-sulfotransferase, comprising the steps of cultivating cultured cells originating from ovary of Chinese hamster in a culture medium, and isolating the heparan sulfate 2-O-sulfotransferase from the medium.

The enzyme of the present invention is conveniently referred to as "heparan sulfate 2-O-sulfotransferase" or "heparan sulfate 2-sulfotransferase". However, it is not meant that the substrate of the enzyme is limited to heparan sulfate. For example, the enzyme of the present invention also transfers sulfate group to the hydroxyl group at C-2 position of iduronic acid residue of CDSNS-heparin. Unmodified heparin has sulfate group at C-2 position of almost all iduronic acid residues. However, heparin having hydroxyl group at that position is present a little. The enzyme of the present invention also transfers sulfate group to the hydroxyl group at C-2 position of iduronic acid residue of such heparin. In this specification, those including modified heparin such as CDSNS-heparin are referred to simply as "heparin", if necessary.

The present invention will be explained in detail below.

<1> Heparan Sulfate 2-Sulfotransferase of the Present Invention

The enzyme of the present invention is an enzyme which has been isolated for the first time according to the present invention, and has the following properties.

(i) Action

Sulfate group is transferred from a sulfate group donor selectively to the hydroxyl group at C-2 position of iduronic acid residue of a sulfate group acceptor. The sulfate group donor is preferably exemplified by activated sulfate (3'-phosphoadenosine 5'-phosphosulfate; hereinafter referred to as "PAPS", if necessary). Sulfate group is scarcely transferred to glucosamine residue. The sulfate group acceptor include heparin and heparan sulfate.

(ii) Substrate Specificity

Sulfate group is transferred to heparan sulfate, heparin or CDSNS-heparin, but sulfate group is not transferred to chondroitin, chondroitin sulfate, dermatan sulfate, and keratan sulfate.

(iii) Optimum Reaction pH

The enzyme of the present invention has a high activity to transfer sulfate group in a range of pH 5 to 6.5, especially in the vicinity of pH 5.5.

(iv) Optimum Ionic Strength

The activity of the enzyme of the present invention increases as the ionic strength increases. In the case of using NaCl, the highest activity is presented at 50 to 200 mM, especially in the vicinity of 100 mM. The activity gradually decreases when the concentration of NaCl increases exceeding the aforementioned range. The activity becomes extremely low at 500 mM.

(v) Inhibition and Activation

The activity of the enzyme of the present invention is increased by protamine. The activity is increased about 3-fold by protamine of about 0.013 mg/ml or more as compared with that in the absence of protamine.

The activity of the enzyme of the present invention is inhibited by 3',5'-ADP.

The activity of the enzyme of the present invention is scarcely affected by DTT at 10 mM or less.

(vi) Michaelis Constant

The enzyme of the present invention has a Michaelis constant (Km) of about 0.20 $\mu$M for PAPS when CDSNS-heparin is used as a sulfate group acceptor and PAPS is used as a sulfate group donor.

(vii) Other Properties

As a result of analysis of an active fraction of the enzyme of the present invention obtained from a culture of cells originating from ovary of Chinese hamster (e.g., CHO cells) by means of sodium dodecyl sulfate-polyacrylamide gel electrophoresis (SDS-PAGE), closely adjoining two broad bands have been found in the vicinity of 44 kDa and 47 kDa. It is not clear whether or not any one of these proteins is the enzyme of the present invention, or both of them are the enzyme of the present invention. In any case, the physical and chemical properties of the enzyme of the present invention described above have been determined by using the enzyme fraction containing the proteins having the broad bands of 44 kDa and 47 kDa. The mobility of the both proteins on electrophoresis was not affected by the presence of mercaptoethanol.

As a result of analysis of the enzyme of the present invention after an N-glycanase (produced by Genzyme) treatment by means of SDS-PAGE, the aforementioned broad bands of 44 kDa and 47 kDa have disappeared, while bands of 34 kDa and 38 kDa have newly appeared. Accordingly, it is suggested that these proteins are glycoproteins containing not less than 19 wt % of sugar.

The enzyme of the present invention was eluted in the vicinity of a molecular weight of about 130,000 on Superose 12 (produced by Pharmacia-LKB) gel chromatography.

The activity to transfer sulfate group of the enzyme of the present invention can be measured by using [$^{35}$S]-PAPS as a sulfate group donor and heparin or heparan sulfate as a sulfate group acceptor, allowing the enzyme of the present invention to act on them, and measuring radioactivity of [$^{35}$S] incorporated into heparin or heparan sulfate. The heparan sulfate O-sulfotransferase activity can be measured by using CDSNS-heparin as a sulfate group acceptor. The heparan sulfate 2-sulfotransferase, which is the enzyme of the present invention, is not inhibited by 10 mM DTT, while the heparan sulfate 6-sulfotransferase, which is a known enzyme, is inhibited by 10 mM DTT. Accordingly, only the heparan sulfate 2-sulfotransferase activity can be measured by adding 10 mM DTT to an enzyme reaction solution containing [$^{35}$S]-PAPS, CDSNS-heparin, and sulfotransferase so that the heparan sulfate 6-sulfotransferase activity is inhibited. When the reaction of the enzyme of the present invention is performed, it is preferable that pH of an enzyme reaction solution is 5 to 6.5, the ionic strength is about 50 to 200 mM (NaCl), and protamine is added in an amount not less than 0.025 mg/ml. Specifically, for example, an enzyme reaction solution (50 µl) containing 2.5 µmol of imidazole hydrochloride (pH 6.8), 3.75 µg of protamine hydrochloride, 25 nmol of CDSNS-heparin, 50 pmol of [$^{35}$S]-PAPS (about 5×10$^5$ cpm), and the enzyme is kept at a temperature of 37° C. for 20 minutes, followed by heating at 100° C. for 1 minute to stop the reaction. Subsequently, 0.1 µmol of chondroitin sulfate A is added as a carrier, and then $^{35}$S-labeled glycosaminoglycan is precipitated by adding cold ethanol containing 1.3% potassium acetate in an amount three times the reaction solution. Further, [$^{35}$S]-PAPS and its decomposed products are removed by desalting, a liquid scintillator is added, and radioactivity of [$^{35}$S] is measured by using a liquid scintillation counter. In the present invention, an activity to transfer 1 pmol of sulfate group per minute under the aforementioned condition is defined as an enzyme amount of 1 unit (U).

<2> Method for Producing the Enzyme of the Present Invention

The enzyme of the present invention having the properties described above can be obtained by cultivating cells originating from animal, for example, cells originating from ovary of Chinese hamster, specifically CHO cells (for example, ATCC CCL61 and the like) in a culture medium, and isolating the heparan sulfate 2-O-sulfotransferase from the medium. CHO cells are preferable as the cultured cells used for cultivation. The enzyme of the present invention may be obtained from cultured cells other than those described above, however, the cultured cells described above are preferred because of good growth properties and possibility of cultivation in a large amount by using suspended cells. The enzyme of the present invention can be also extracted from the medium after cultivation. The enzyme of the present invention may be used as a crude enzyme when it contains no other sulfotransferase activity, or when other contaminating sulfotransferase activities can be effectively suppressed.

The medium to be used for the cultivation of the cultured cells described above is not specifically limited, however, it is preferable to use those suitable for floating cells contained in, for example, a spinner flask in order to efficiently obtain a large amount of cells. Specifically, a commercially available medium may be used, such as CHO-S-SFMII medium (produced by Gibco) developed for suspended culture for CHO cells.

In order to avoid growth of microorganisms, it is preferable to add antibiotics such as penicillin and streptomycin to the medium. When the medium as described above is used to conduct cultivation in the same manner as ordinary cultured cells by using roller bottles, dishes or the like, the enzyme of the present invention is accumulated in the culture, especially in cultured cells.

The enzyme of the present invention can be purified by using a starting material such as a supernatant after centrifugation obtained by collecting cells from a culture after cultivation by means of, for example, centrifugation, disrupting cells by means of, for example, homogenization, ultrasonic treatment, or osmotic pressure shock, and centrifuging a cell-disrupted solution obtained by the preceding step. The enzyme of the present invention can be purified by means of affinity chromatography by using a Heparin-Sepharose CL-6B (produced by Pharmacia) column, a 3',5'-ADP-agarose column and the like, or gel filtration chromatography by using a Superose 12 (produced by Pharmacia) column. Additionally, the enzyme can be purified by using known enzyme purification methods such as ion exchange chromatography, gel filtration, electrophoresis, hydrophobic chromatography, and salting out, if necessary.

The enzyme of the present invention may be also obtained by using transformed cells obtained by isolating a gene coding for the enzyme of the present invention from the cultured cells described above, and introducing it into other cultured cells or microbial cells.

The enzyme of the present invention has enabled enzymatic selective introduction of sulfate group into the hydroxyl group at C-2 position of iduronic acid residue contained in heparin and heparan sulfate. The heparan sulfate 2-sulfotransferase introduces sulfate group selectively into C-2 position of iduronic acid residue of heparin and heparan sulfate extremely strictly. Accordingly, it is expected to exploit the enzyme for reagents useful for studies such as functional analysis of heparin and heparan sulfate.

Considering creation of heparin and heparan sulfate having new physiological activities unknown at present and application as pharmaceuticals by using the enzyme of the present invention to selectively introduce sulfate group into C-2 position of iduronic acid residue of heparan sulfate, it can be expected to create heparin or heparan sulfate having physiological activities preferable for human. Since it is known that the degree of sulfation of heparan sulfate decreases in accordance with malignant alteration, it is also expected to enable the amount of the enzyme to be related to malignant alteration of cells by producing an antibody against the enzyme of the present invention and detecting the enzyme of the present invention in tissues.

DESCRIPTION OF PREFERRED EMBODIMENT

Figure 1:
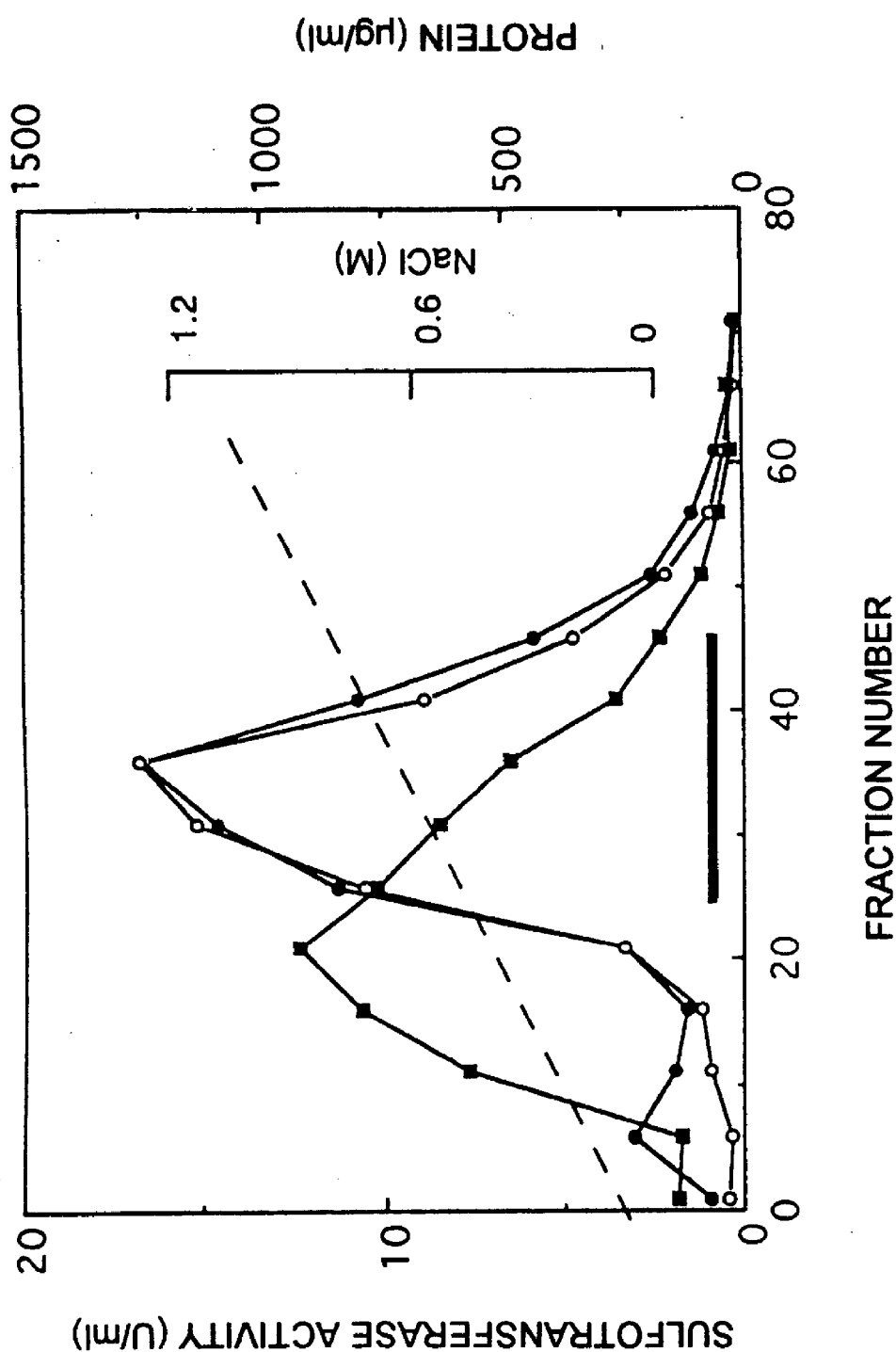
FIG. 1 shows a result of first Heparin-Sepharose CL-6B chromatography for the enzyme of the present invention. Closed circles indicate heparan sulfate O-sulfotransferase activity (the activity was measured in the absence of DTT), open circles indicate heparan sulfate 2-sulfotransferase activity (the activity was measured in the presence of 10 mM DTT), closed squares indicate protein concentration, and a broken line indicates NaCl concentration.

Embodiments of the present invention will be described below. Available sources and methods for obtaining reagents and samples used in the embodiments are described below.

$[^{35}S]$-$H_2SO_4$ was purchased from Japan Isotope Association. CHO-S-SFMII medium was purchased from Gibco. PAPS, 3',5'-ADP-agarose, and heparin were purchased from Sigma. Cosmedium-001 medium was purchased from Cosmo Bio. Polyethylene glycol #20000 was purchased from Nacalai Tesque. Fast desalting column, Heparin-Sepharose CL-6B, Superose 12 column, and Superdex 30 pg column were purchased from Pharmacia-LKB. PAMN column (silica column with bound polyamine) was purchased from YMC. Partisil-10 SAX column was purchased from Whatman. Chondroitinase ABC, heparitinase I, II, III, chondroitin sulfate A (from whale cartilage, 4S/6S:80/20), CDSNS-heparin, chondroitin sulfate C (from shark cartilage, 4S/6S:10/90), dermatan sulfate, keratan sulfate, and a kit of unsaturated disaccharides from glycosaminoglycan were purchased from Seikagaku Corporation. $[^{35}S]$-PAPS was prepared in accordance with a method described by Delfert, D. M. and Conrad, E. H. (1985) in *Anal. Biochem.*, 148, 303–310. Chondroitin (from squid skin) was prepared in accordance with a method described by Habuchi, O. and Miyata, K. (1980) in *Biochim. Biophys. Acta*, 616, 208–217. p-Tosyl-L-lysine-chloromethyl ketone was purchased from Aldrich. Phenylmethylsulfonylfluoride and N-tosyl-L-phenylalanine-chloromethyl ketone were purchased from Sigma. Pepstatin was purchased from Wako Pure Chemical Industries. Heparan sulfate from mouse EHS (Engelbreth-Holm-Swarm) tumor, heparan sulfate from swine aorta, and heparan sulfate from bovine liver were obtained from Seikagaku Corporation.

<1> Method for Measuring Activity of Sulfotransferase Enzyme (1) Measurement of Sulfotransferase Activity The enzyme activity was measured in accordance with a method described below in purification steps of the heparan sulfate 2-sulfotransferase, analysis of properties of the enzyme and so on.

An enzyme reaction solution was a mixture (50 μl) which contained 2.5 μmol of imidazole hydrochloride (pH 6.8), 3.75 μg of protamine hydrochloride, CDSNS-heparin (25 nmol as converted into an amount of hexosamine), 50 pmol of $[^{35}S]$-PAPS (about $5\times10^5$ cpm), and the enzyme. This reaction solution was kept at a temperature of 37° C. for 20 minutes, followed by heating at 100° C. for 1 minute to stop the reaction. Subsequently, chondroitin sulfate A (0.1 μmol as converted into an amount of glucuronic acid) was added as a carrier, and then $^{35}$S-glycosaminoglycan was precipitated by adding cold ethanol containing 1.3% potassium acetate in an amount three times the reaction solution. Further, [35S]-PAPS and its decomposed products were completely separated by using a fast desalting column as described in Habuchi, O. et al., (1993) *J. Biol. Chem.*, 2, 21968–21974. A liquid scintillator (Ready Safe Scintillator, produced by Beckman) was mixed therewith, and radioactivity was measured by using a liquid scintillation counter to calculate the amount of transferred sulfate group. An activity to transfer 1 pmol of sulfate group per minute under the aforementioned condition was defined as an enzyme amount of 1 unit (U).

The heparan sulfate O-sulfotransferase activity was measured by using CDSNS-heparin as a sulfate group acceptor as described above. The heparan sulfate 2-sulfotransferase activity was measured by inhibiting the heparan sulfate 6-sulfotransferase activity by adding 10 mM DTT to the enzyme reaction solution described above, if necessary.

(2) Measurement of Content of Galactosamine and Glucosamine in Glycosaminoglycan Content of galactosamine and glucosamine in glycosaminoglycan was measured by an Elson-Morgan method after hydrolyzing the glycosaminoglycan in 6M HCl at 100° C. for 4 hours.

<2> Distribution of Heparan Sulfate 6-Sulfotransferase and Heparan Sulfate 2-Sulfotransferase in Cultured CHO Cells In order to investigate distribution of heparan sulfate 6-sulfotransferase and heparan sulfate (HexA) 2-sulfotransferase (sulfate group is transferred to the hydroxyl group at C-2 position of hexuronic acid (HexA) residue) in cultured CHO cells, the following experiment was performed.

CHO cells (ATCC CCL61) were cultivated for 48 hours in Cosmedium-001 medium. After that, the sulfotransferase activity was measured for the medium and an extract solution from cells (supernatant obtained by homogenizing cells with buffer A (10 mM Tris-HCl, pH 7.2, 10 mM $MgCl_2$, 2 mM $CaCl_2$, 20% glycerol, 0.1% Triton X-100) containing 0.15M NaCl, raising the concentration of Triton X-100 to 0.5%, and performing extraction for 1 hour with agitation followed by centrifugation at 10,000×g for 30 minutes) by using CDSNS-heparin as a substrate and [$^{35}$S]PAPS as a sulfate group donor. As a result, as shown in Table 1, not less than 95% of the heparan sulfate (HexA) 2-sulfotransferase was present in cells, and only not more than 5% of it was present in the medium. In Table 1, the heparan sulfate (HexA) 2-sulfotransferase is simply expressed as "2-sulfotransferase".

TABLE 1

| Heparan sulfate sulfotransferase | Sulfotransferase activity (units/5.4 × 10$^7$ cells) | |
|---|---|---|
| | Cell | Medium |
| 6-Sulfotransferase | 1.5 | 14.0 |
| 2-Sulfotransferase | 17.0 | 0.6 |
| Total sulfotransferase | 18.5 | 14.6 |

On the other hand, as already reported by the present inventors, not less than 90% of heparan sulfate 6-sulfotransferase was present in the medium. According to these observations, it has been demonstrated that purification of the heparan sulfate 2-sulfotransferase as the enzyme of the present invention is preferably started from an extract solution obtained from CHO cells.

<3> Purification of Heparan Sulfate 2-Sulfotransferase Produced by CHO Cells (1) Cultivation of CHO Cells and Preparation of Crude Extract CHO cells (ATCC CCL61) were inoculated to CHO-S-SFMII medium (10 ml) containing 50 μg/ml of streptomycin and 50 units of penicillin (1 ml) at a cell density of 2×10$^6$ cells/100 mm dish, and cultivated for 4 days. After that, cultured cells were inoculated to CHO-S-SFMII medium (500 ml) at a cell density of 3.0×10$^5$ cells/ml, and cultivated in a suspended state in a spinner flask (produced by Techne) for 4 days while agitating at 90 rpm. An obtained culture liquid was centrifuged at 1,000×g for 5 minutes to collect cells and the cells were then washed with cold phosphate buffer (PBS (−)). In order to extract sulfotransferase from the cells, extraction buffer (10 mM Tris-HCl, pH 7.2, 0.5% w/v Triton X-100, 10 mM $MgCl_2$, 2 mM $CaCl_2$, 0.15M NaCl, 20% v/v glycerol, four types of protease inhibitors (5 μM p-tosyl-L-lysine-chloromethyl ketone, 3 μM N-tosyl-L-phenylalanine-chloromethyl ketone, 30 μM phenylmethylsulfonylfluoride, and 3 μM pepstatin) was added in an amount of 55 ml for 1×10$^9$ cells. The cells in the extraction buffer were homogenized 10 times by using a glass homogenizer, followed by agitation at 4° C. for 1 hour. An extract solution was centrifuged at 10,000×g for 30 minutes to obtain a supernatant. The supernatant was used as a crude extract and pooled (1.8 L), and the crude extract was stored at −20° C. until purification was started.

(2) Purification of Heparan Sulfate 2-Sulfotransferase

All of the following operations were performed at 4° C.

(i) First step: first Heparin-Sepharose CL-6B chromatography

One third of the crude extract (600 ml) prepared as described above was applied to a column (30×70 mm, 50 ml) of Heparin-Sepharose CL-6B equilibrated with buffer A containing four types of protease inhibitors (p-tosyl-L-lysine-chloromethyl ketone (5 μM), N-tosyl-L-phenylalanine-chloromethyl ketone (3 μM), phenylmethyl-sulfonylfluoride (30 μM), and pepstatin (3 μM)) and 0.15M NaCl. The flow rate was 76 ml/hour. The column was washed with buffer A containing the four types of the protease inhibitors and 0.15M NaCl in an amount ten times the column volume to remove a fraction not adsorbed to the column, and then an adsorbed fraction was eluted with a linear concentration gradient (total volume 1,000 ml) in which the NaCl concentration was increased from 0.15M to 1.2M in buffer A containing the four types of the protease inhibitors and NaCl. Thus fractions (13 ml each) were collected. Each of the eluted fractions was measured for the protein concentration, the sulfotransferase activity in the presence of 10 mM DTT (heparan sulfate 2-sulfotransferase activity), and the sulfotransferase activity in the absence of DTT (heparan sulfate O-sulfotransferase activity) (FIG. 1). Fractions containing the sulfotransferase activity (corresponding to portion indicated by a thick line in FIG. 1) were pooled, and the pooled fractions were introduced into a dialysis tube. Powder of polyethylene glycol #20000 was sprinkled thereto to perform concentration up to about 100 ml. The concentration of Triton X-100 was adjusted to be 1%, followed by dialysis against buffer A containing 0.05M NaCl for the next purification step.

Owing to the operation described above, the heparan sulfate 2-sulfotransferase activity increased about 1.9-fold. This may be caused by elimination of degrading enzymes for PAPS and substances inhibiting for heparan sulfate 2-sulfotransferase activity through the column chromatography.

(ii) Second step: 3',5'-ADP-agarose chromatography

The dialyzed solution obtained in the first step described above was passed through a 3',5'-ADP-agarose column (14×90 mm, 15 ml) equilibrated with buffer A containing 0.05M NaCl. The flow rate was 13 ml/hour. The column was washed with buffer A containing 0.05M NaCl in an amount eight times the column volume to remove a fraction not adsorbed to the column, and then an adsorbed fraction was eluted with buffer A containing 0.05M NaCl and 0.2 mM 3',5'-ADP in an amount five times the column volume. Buffer A containing 1M NaCl was added to the fraction so that the final concentration of NaCl became 0.15M.

A combination of the first and second steps was repeated three times. Active fractions obtained by the three times of operations were pooled. An aliquot of the pooled fraction was applied to a small column of Heparin-Sepharose (bed volume: 0.6 ml), and the column was washed with buffer A containing 0.15M NaCl, followed by elution with buffer A containing 1.0M NaCl. An obtained fraction was measured for its activity to determine a total activity of the enzyme purified at this stage.

Owing to the operation described above, the specific activity of the heparan sulfate 2-sulfotransferase became 44-fold at one step, revealing that the operation was an extremely effective method for purification of this enzyme.

(iii) Third step: second Heparin-Sepharose CL-6B chromatography

Figure 2:
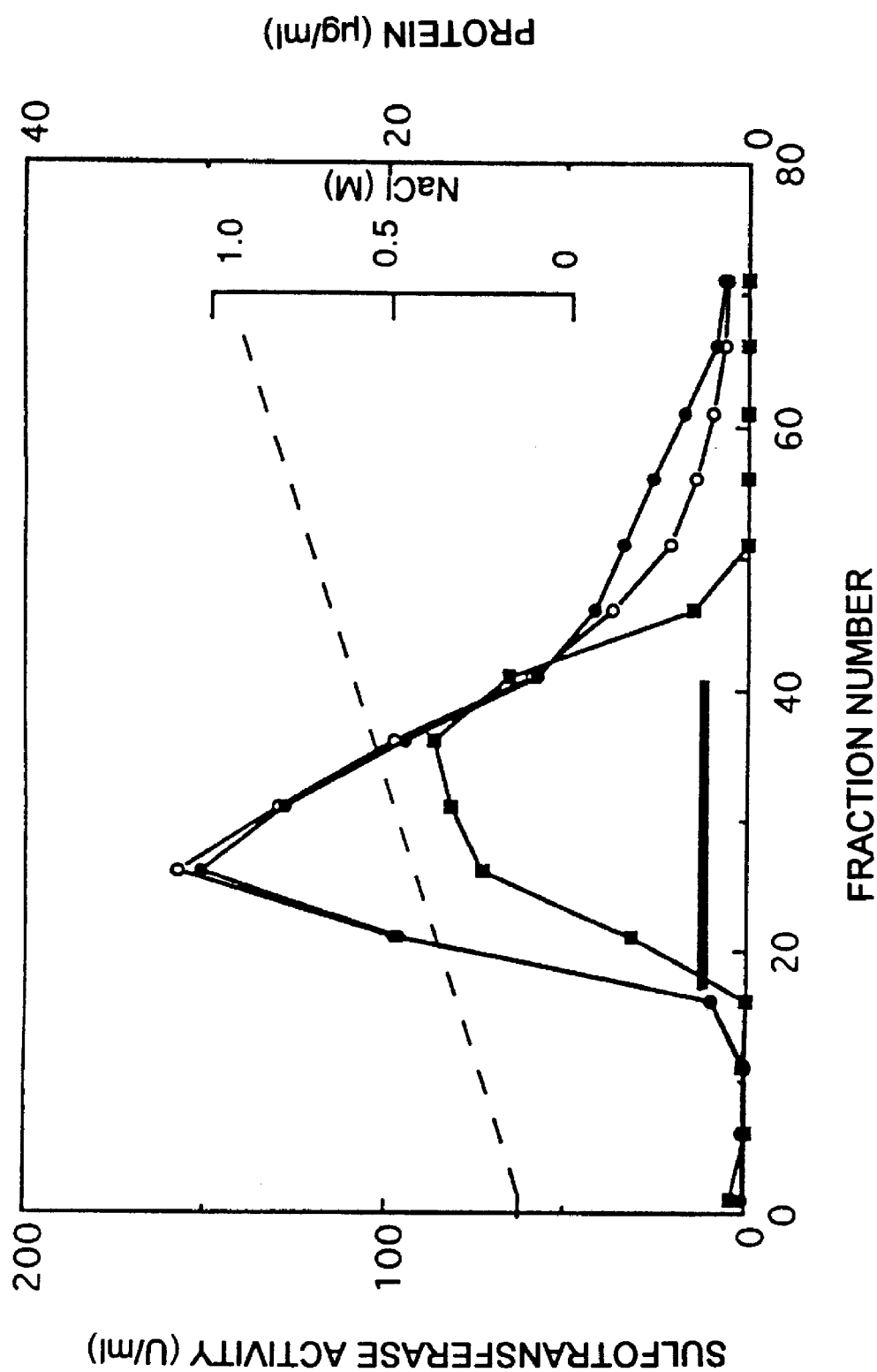
FIG. 2 shows a result of second Heparin-Sepharose CL-6B chromatography for the enzyme of the present invention. Closed circles, open circles, closed squares and a broken line in FIG. 2 indicate the same as those in FIG. 1 respectively.

The active fraction of the heparan sulfate 2-sulfotransferase obtained in the second step was applied to a Heparin-Sepharose CL-6B column (16×50 mm, 10 ml) equilibrated with buffer A containing 0.15M NaCl. The column was washed with buffer A containing 0.15M NaCl in an amount five times the column volume, and then an adsorbed fraction was eluted with a linear concentration gradient (total volume: 300 ml) in which the NaCl concentration was increased from 0.15M to 1.0M in the buffer. The protein concentration, the sulfotransferase activity in the presence of 10 mM DTT (heparan sulfate 2-sulfotransferase activity), and the sulfotransferase activity in the absence of DTT (heparan sulfate O-sulfotransferase activity) of each of eluted fractions were measured. Results are shown in FIG. 2.

Among the fractions containing the heparan sulfate 2-sulfotransferase activity obtained as described above, fractions shown by a thick line in FIG. 2 were collected. The concentration of Triton X-100 was raised to 1%, followed by dialysis against buffer A containing 1M NaCl, and followed by dialysis against buffer A containing 0.05M NaCl.

(iv) Fourth step: second 3',5'-ADP-agarose chromatography

The fraction obtained in the third step was applied to a 3',5'-ADP-agarose column in the same manner as done in the first chromatography to perform chromatography. As a result of the chromatography, the degree of purification was increased 11-fold, and the specific activity was 26,700-fold at this stage. The NaCl concentration of a fraction eluted with buffer A containing 0.2 mM 3',5'-ADP and 0.05M NaCl was adjusted to be 0.15M, and then the fraction was concentrated to 8 ml by using polyethylene glycol in the same manner as described above. The concentrate was dialyzed against buffer A containing 0.1M NaCl, and was thereafter applied to a small Heparin-Sepharose column (bed volume: 0.6 ml). The column was washed with buffer B (identical with buffer A except that only the concentration of Triton X-100 was changed to 0.02%) containing 0.1M NaCl, followed by elution with buffer B containing 1M NaCl (2.5 ml). This eluted solution was concentrated to 0.5 ml, and the concentrate was used for the next purification step.

(v) Fifth step: Superose 12 gel chromatography

Figure 3:
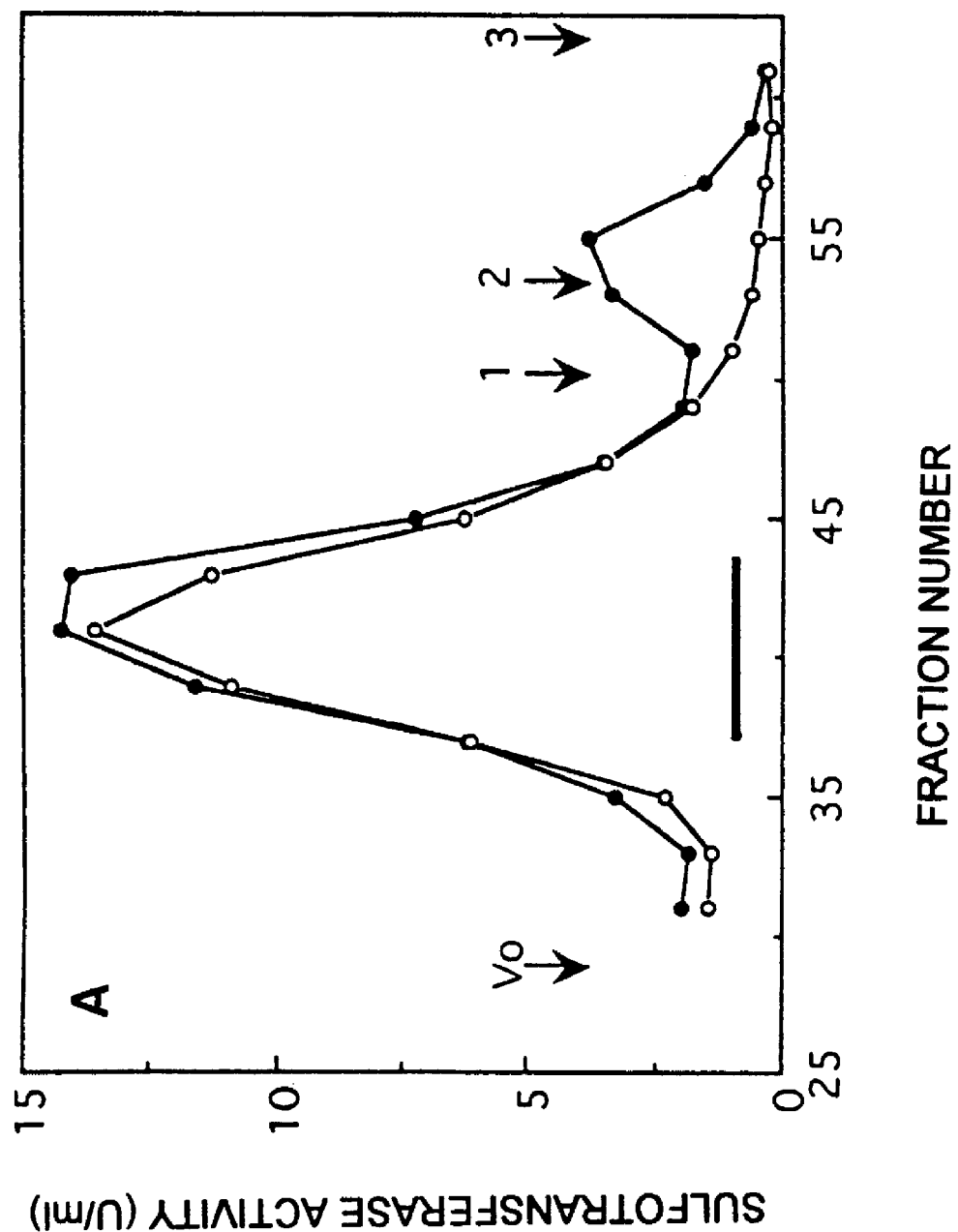
FIG. 3 shows a result of Superose 12 gel chromatography. Closed circles and open circles in FIG. 3 indicate the same as those in FIG. 1 respectively. Arrows with numerals 1, 2, and 3 in FIG. 3 indicate positions of elution of standard proteins respectively. 1: bovine serum albumin (BSA; 67 kDa), 2: ovalbumin (43 kDa), 3: chymotrypsinogen (25 kDa).

The fraction obtained in the fourth step was applied to a Superose 12 column equilibrated with buffer A containing 2M NaCl. Chromatography was performed at a flow rate of 0.25 ml/minute to fractionate into each fraction of 0.25 ml. Each of the eluted fractions was measured for the sulfotransferase activity in the presence of 10 mm DTT (heparan sulfate 2-sulfotransferase activity) and the sulfotransferase activity in the absence of DTT (heparan sulfate O-sulfotransferase activity). A major activity of the sulfotransferase was eluted in the vicinity of a molecular weight of 130,000 (peak on a side of high molecular weight in FIG. 3 (Peak I)). On the other hand, a minor activity, which was inhibited by DTT, was eluted in the vicinity of a molecular weight of 42,000 (peak on a side of low molecular weight (Peak II)). Heparan sulfate 2-sulfotransferase is not inhibited by DTT, but heparan sulfate 6-sulfotransferase is inhibited by DTT. Accordingly, the peak in the vicinity of the molecular weight of 42,000 seems to be heparan sulfate 6-sulfotransferase. In addition, this molecular weight is well coincident with a molecular weight of heparan sulfate 6-sulfotransferase described in a paper previously reported by the present inventors. Further, a heparitinase-digest of CDSNS-heparin $^{35}$S-labeled by using the fraction of Peak II contained ΔDi-(N,6)diS as a major component. Fractions containing sulfotransferase activity not inhibited by DTT (corresponding to portion depicted by a thick line in FIG. 3) were pooled, dialyzed against buffer A containing 0.15M NaCl, and stored at −20° C.

Figure 4:
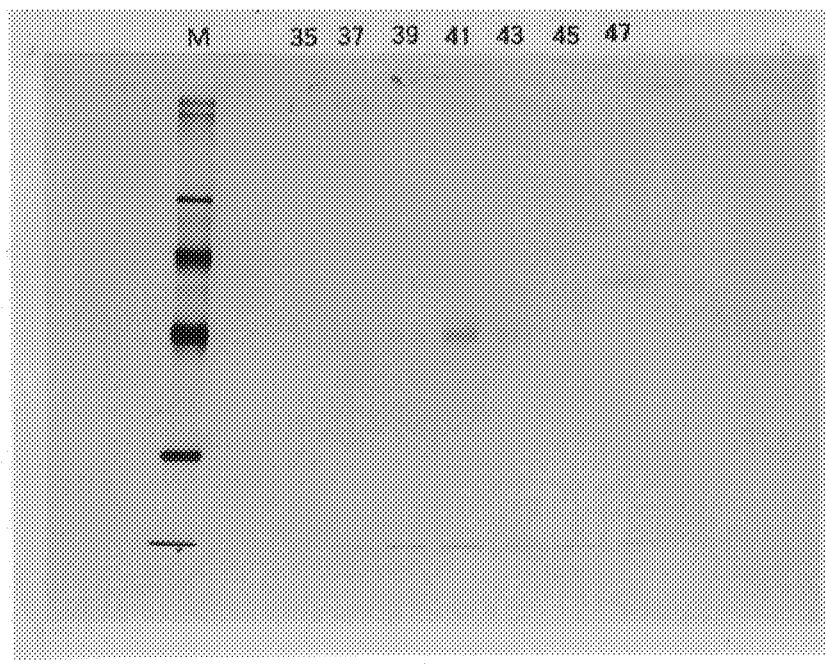
FIG. 4 is an electrophoretic photograph which shows a result of SDS-PAGE of fractions fractionated by the Superose 12 gel chromatography. Numbers at upper portions in FIG. 4 indicate fraction numbers. M indicates molecular weight markers.

As described above, the heparan sulfate 2-sulfotransferase was purified about 51,700-fold to the crude extract by the purification process of five steps, and it gave approximately homogeneous two bands on SDS-PAGE as described below (FIG. 4). The degree of purification in each of the steps is shown in Table 2.

TABLE 2

| Purification step | Volume (ml) | Total activity (× 10³ U) | Total protein (mg) | Specific activity (× 10⁴ U/mg) | Purification degree (-fold) | Yield (%) |
|---|---|---|---|---|---|---|
| Crude extract | 1,800 | 20.0 | 4,560 | 0.000439 | 1 | 100 |
| 1st Heparin-Sepharose | 300 | 37.5 | 390 | 0.00962 | 22 | 188 |
| 1st 3',5'-ADP-agarose | 225 | 23.6 | 5.60 | 0.421 | 959 | 118 |
| 2nd Heparin-Sepharose | 96 | 12.9 | 1.22 | 1.06 | 2,420 | 65 |
| 2nd 3',5'-ADP-agarose | 75 | 4.75 | 0.0405 | 11.7 | 26,700 | 24 |
| Superose 12 | 1.75 | 1.24 | 0.0055 | 22.7 | 51,700 | 6 |

(3) Analysis of Purified Enzyme by SDS-PAGE

Figure 5:
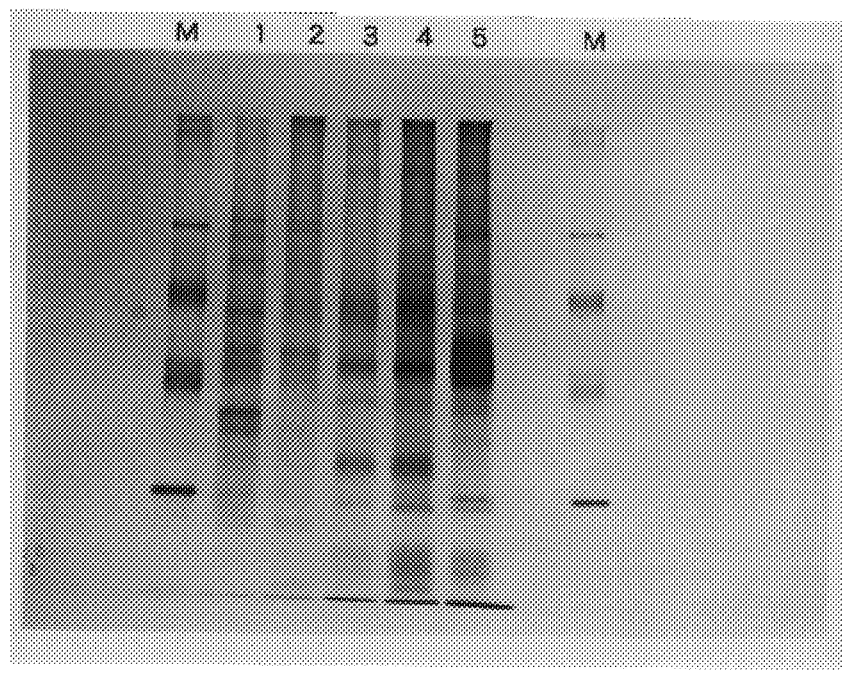
FIG. 5 is an electrophoretic photograph which shows a result of SDS-PAGE of enzyme fractions of the present invention in each of purification steps. M: molecular weight markers, lane 1: crude extract, lane 2: fraction corresponding to a portion indicated by a horizontal line (thick line) in FIG. 1 in the first Heparin-Sepharose CL-6B, lane 3: adsorbed fraction in the first 3',5'-ADP agarose, lane 4: fraction corresponding to a portion indicated by a horizontal line (thick line) in FIG. 2 in the second Heparin-Sepharose CL-6B chromatography, lane 5: adsorbed fraction in the second 3',5'-ADP agarose.

The purified enzyme of heparan sulfate 2-sulfotransferase and samples in each of the steps of purification obtained as described above were subjected to SDS-PAGE by using 10% gel in accordance with a method of Laemmli (Laemmli, U. K. (1970) *Nature,* 227, 680–685). Bands of proteins were detected by silver staining. A result of SDS-PAGE of the purified enzyme is shown in FIG. 4. A result of SDS-PAGE of the samples in each of the purification steps is shown in FIG. 5. Closely adjoining broad bands of about 44 kDa and about 47 kDa were principally found in the fraction obtained by Superose 12 gel chromatography (FIG. 4). Judging from the elution pattern of the enzyme activity, the two extremely closely adjoining bands having the molecular weights of about 44 kDa and about 47 kDa seem to coincide with the heparan sulfate 2-sulfotransferase.

Next, it was investigated whether or not the sugar chain was present in the heparan sulfate 2-sulfotransferase protein. The enzyme protein was precipitated by adding TCA (trichloroacetic acid) to a heparan sulfate 2-sulfotransferase solution containing 0.15 μg of the protein so that the final concentration became 10%. The precipitate was recovered by centrifugation. The precipitate was washed with acetone and dried, and then kept at a temperature of 37° C. for 16 hours in a reaction solution described below.

The reaction solution contained 0.05M Tris-HCl, pH 7.8 containing 0.5% sodium dodecyl sulfate (SDS) (10 μl); 7.5% (w/v) Nonidet P-40 (5 μl); 0.25M EDTA (1.2 μl); phenylmethylsulfonylfluoride (0.3 μl); and 0.5 unit of N-glycanase (recombinant N-glycanase: produced by Genzyme).

Figure 6:
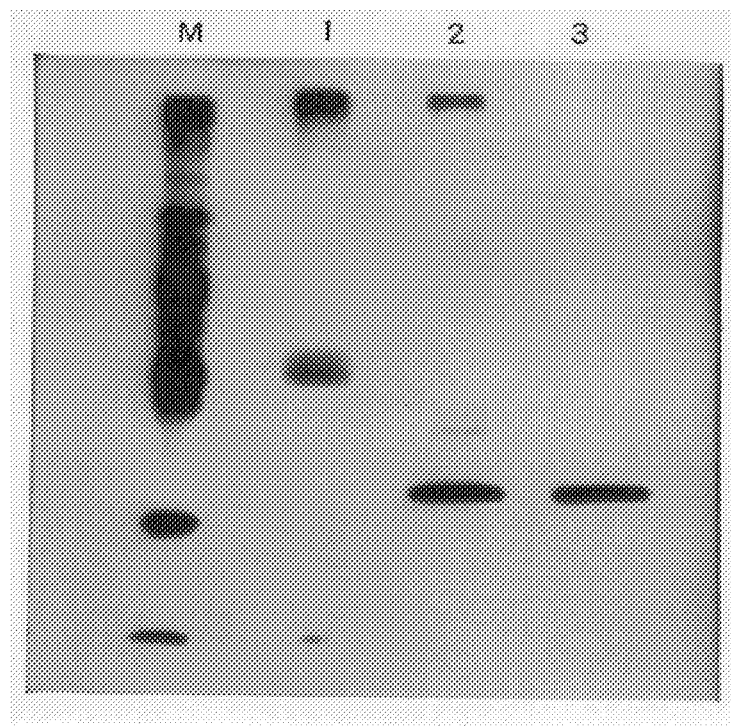
FIG. 6 is an electrophoretic photograph which shows a result of SDS-PAGE of the enzyme of the present invention subjected to or not subjected to an N-glycanase treatment. Lane 1: the enzyme of the present invention not subjected to the treatment, lane 2: the enzyme of the present invention treated with N-glycanase, lane 3: N-glycanase.

As a result of analysis of the reaction solution described above by means of SDS-PAGE, the closely adjoining protein bands of 44 kDa and 47 kDa disappeared, and protein bands of 34 kDa and 38 kDa appeared (FIG. 6). According to this result, it is suggested that the proteins of the both bands are glycoproteins containing not less than 19 wt % of sugar.

(4) Substrate Specificity and Action of Heparan Sulfate 2-Sulfotransferase

In order to investigate the substrate specificity of the heparan sulfate 2-sulfotransferase of the present invention, the activity to transfer $^{35}$S-sulfate group from [$^{35}$S]-PAPS was measured by using the purified enzyme and using various substrates (25 nmol) as acceptors. Results are shown in Table 3. Numbers in parentheses in the table indicate the activity to transfer sulfate group with respect to each of the acceptors when the activity to transfer sulfate group using CDSNS-heparin as the acceptor is regarded to be 100.

TABLE 3

| Substrate | Purified enzyme activity, U/ml |
|---|---|
| CDSNS-heparin | 7.19 (100) |
| Heparan sulfate | |
| from mouse EHS tumor | 6.59 (92) |
| from swine aorta | 0.81 (11) |
| from bovine liver | 1.12 (16) |
| Chondroitin | 0 |
| Chondroitin sulfate A | 0.05 (0.7) |
| Chondroitin sulfate C | 0 |
| Dermatan sulfate | 0 |
| Keratan sulfate | 0 |

The heparan sulfate 2-sulfotransferase of the present invention transferred sulfate group to CDSNS-heparin and heparan sulfate originating from EHS tumor, and more weakly transferred sulfate group to heparan sulfate originating from swine aorta and bovine liver. However, no transfer was observed with respect to chondroitin, chondroitin sulfate A and C, dermatan sulfate, and keratan sulfate.

In order to investigate the position of sulfate group transferred by the heparan sulfate 2-sulfotransferase of the present invention by using CDSNS-heparin and heparan sulfate from EHS tumor as acceptors and using [$^{35}$S]-PAPS as a sulfate group donor, transfer reaction products were digested with 50 μl of a mixed solution containing about 25 nmol of reaction product, 50 mM Tris-HCl (pH 7.2), 1 mM CaCl$_2$, 2 μg bovine serum albumin (BSA), 10 mU heparitinase I, 1 mU heparitinase II, and 10 mU heparitinase III at 37° C. for 2 hours.

The digest was separated together with standard unsaturated disaccharides in accordance with a known method (Habuchi, H. et al., (1992) *Biochem. J.*, 285, 805–813) by using HPLC (high performance liquid chromatography, column: silica column with bound polyamine (PAMN column)), fractionated into each aliquot of 0.6 ml, and mixed with 3 ml of liquid scintillator (Ready Safe Scintillator, produced by Beckman) to measure radioactivity by using a liquid scintillation counter. Heparitinase is an enzyme which cuts α-N-acetyl/-sulfo-D-glucosaminyl (1→4) uronic acid bond of heparan sulfate in a manner of an elimination reaction to produce oligosaccharides having Δ$^4$-hexuronic acid at the non-reducing end thereof.

Figure 7:
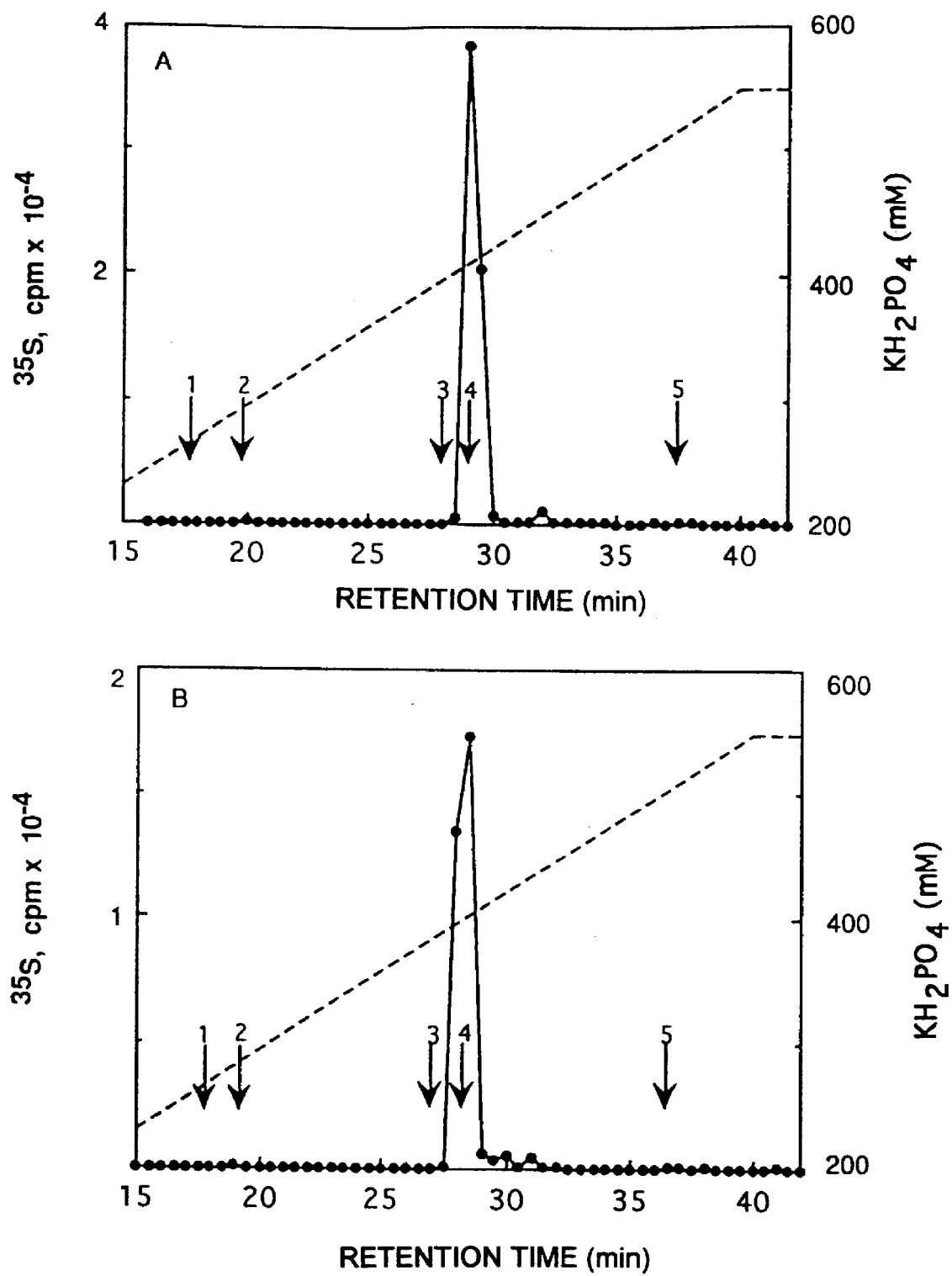
FIG. 7 shows HPLC chromatograms of heparitinase-digested reaction products obtained by sulfate group transfer to (A) CDSNS-heparin and (B) heparan sulfate originating from EHS tumor by using the enzyme of the present invention. Closed circles and a broken line indicate radioactivity and $KH_2PO_4$ concentration, respectively.

Results are shown in FIG. 7 (A: CDSNS-heparin as a substrate, B: heparan sulfate from EHS tumor as a substrate). In FIG. 7, arrows with reference numerals 1 to 5 indicate positions of elution of unsaturated disaccharides shown below (see Formula 1 and Table 4). "ΔDiHS" indicates unsaturated disaccharide produced by digestion of heparin and heparan sulfate by heparitinase. "6,N" indicates a position of sulfation of glucosamine. "U" indicates that C-2 position of uronic acid is sulfated.

1: ΔDiHS-6S
2: ΔDiHS-NS
3: ΔDiHS-di(6,N)S
4: ΔDiHS-di(U,N)S
5: ΔDiHS-tri(U,6,N)S

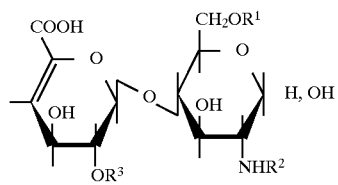

TABLE 4

| Unsaturated disaccharide residue | R$^1$ | R$^2$ | R$^3$ |
|---|---|---|---|
| ΔDiHS-6S | SO$_3$— | Ac | H |
| ΔDiHS-NS | H | SO$_3$— | H |
| ΔDiHS-di(6,N)S | SO$_3$— | SO$_3$— | H |
| ΔDiHS-di(U,N)S | H | SO$_3$— | SO$_3$— |
| ΔDiHS-tri(U,6,N)S | SO$_3$— | SO$_3$— | SO$_3$— |

As a result, when CDSNS-heparin was used as an acceptor, almost all of the radioactivity coincided with the elution position of standard ΔDiHS-di(U,N)S (FIG. 7A). On the other hand, when heparan sulfate from EHS tumor was used as an acceptor, almost all of the radioactivity also coincided with the elution position of standard ΔDiHS-di(U,N)S (FIG. 7B) similarly.

Figure 8:
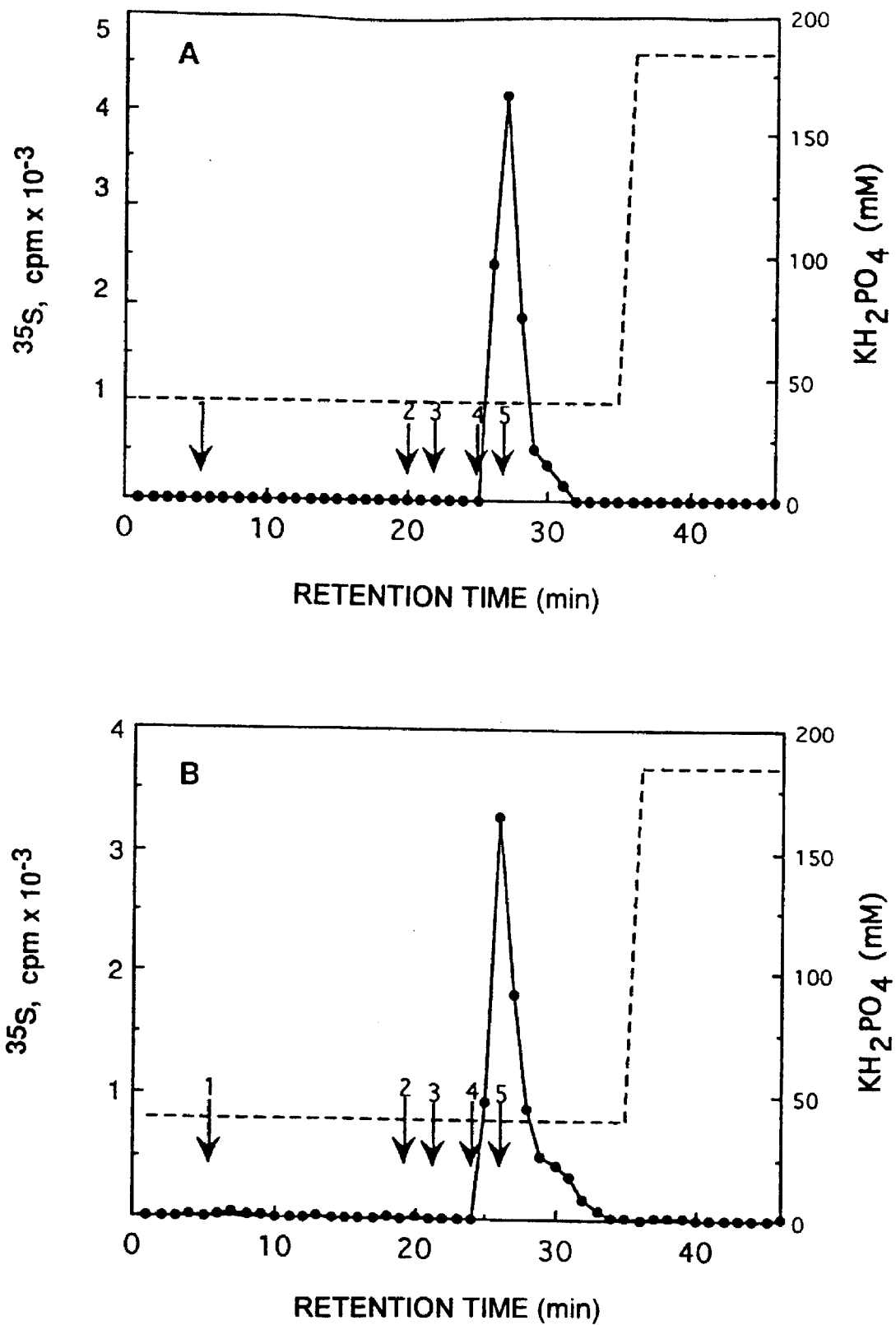
FIG. 8 shows HPLC chromatograms of disaccharides eluted by using a Partisil-10 SAX column, the disaccharides being produced by decomposing, with nitrite at pH 1.5, reaction products obtained by sulfate group transfer to (A) CDSNS-heparin and (B) heparan sulfate originating from EHS tumor by using the enzyme of the present invention, and reducing with $NaBH_4$. Closed circles and a broken line indicate the same as those in FIG. 7.

Further, the CDSNS-heparin and the heparan sulfate from EHS tumor which were $^{35}$S-labeled as described above were decomposed with nitrite at pH 1.5, and then reduced with NaBH$_4$ to obtain disaccharide fractions, and the fractions were analyzed by HPLC by using a Partisil-10 SAX column respectively. A result of analysis of the disaccharide fraction originating from CDSNS-heparin is shown in FIG. 8A. A result of analysis of the disaccharide fraction originating from heparan sulfate from EHS tumor is shown in FIG. 8B. In FIGS. 8A and 8B, arrows with reference numerals 1 to 5 indicate elution positions of disaccharides described below. "AMan" indicates 2,5-anhydro-D-mannose, and "R" indicates alditol obtained by reduction with NaBH$_4$. "(2SO$_4$)" indicates that C-2 position is sulfated. "(6SO$_4$)" indicates that C-6 position is sulfated.

1: HexA-AMan$_R$
2: GlcA(2SO$_4$) -AMan$_R$
3: GlcA-AMan$_R$(6SO$_4$)
4: IdoA-AMan$_R$(6SO$_4$)
5: IdoA(2SO$_4$)-AMan$_R$

As a result, regardless of whichever acceptor to be used, almost all of the radioactivity coincided with the elution position of IdoA(2SO$_4$)-AMan$_R$.

According to the results described above, it has been demonstrated that the heparan sulfate 2-sulfotransferase of the present invention transfers sulfate group to the hydroxyl group at C-2 position of iduronic acid residue adjacent to N-sulfoglucosamine residue. Sulfation of glucosamine residue by the enzyme of the present invention was not observed.

Figure 9:
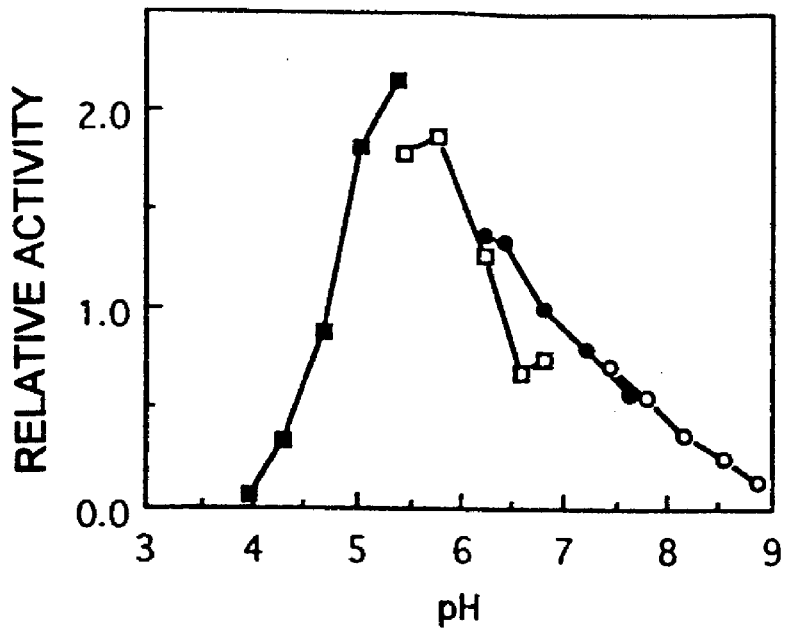
FIG. 9 shows pH-enzyme activity curves demonstrating optimum pH of the enzyme of the present invention. Open circles indicate Tris-HCl buffer, closed circles indicate imidazole-HCl buffer, open squares indicate 2-(N-morpholino)ethanesulfonic acid (MES) buffer, and closed squares indicate potassium acetate buffer.

(5) Other Enzymatic Properties of Heparan Sulfate 2-Sulfotransferase
(i) Optimum pH
Optimum pH of the enzyme of the present invention was measured. As buffers, 50 mM Tris-HCl, 50 mM imidazole-HCl, 50 mM MES buffer (produced by Nacalai Tesque), and 50 mM potassium acetate buffers were used to measure the enzyme activity at various pH's. Relative activities with respect to an enzyme activity in imidazole-HCl buffer (pH 6.8) are respectively shown in FIG. 9. As a result, the enzyme of the present invention exhibited high enzyme activities at about pH 5 to 6.5. A maximum activity was obtained at about pH 5.5.

(ii) Optimum Ionic Strength

Figure 10:
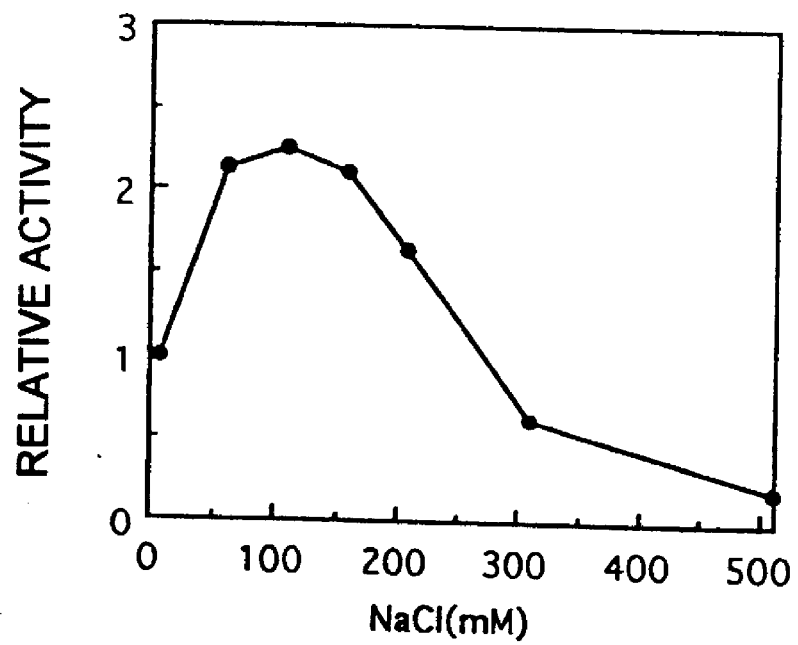
FIG. 10 shows an NaCl concentration-enzyme activity curve demonstrating optimum NaCl concentration of the enzyme of the present invention.

In order to investigate the influence of ionic strength on the activity of the enzyme of the present invention, NaCl was added to the enzyme reaction solution at various concentrations to investigate the enzyme activity. A result is shown in FIG. 10. According to the result, the enzyme of the present invention exhibited high enzyme activities in the vicinity of 50 to 200 mM NaCl. A maximum activity was observed at about 100 mM NaCl. This property is different from that of N-sulfotransferase whose activity is inhibited in an NaCl concentration-depending manner.

(iii) Inhibition and Activation of the Enzyme of the Present Invention

Figure 11:
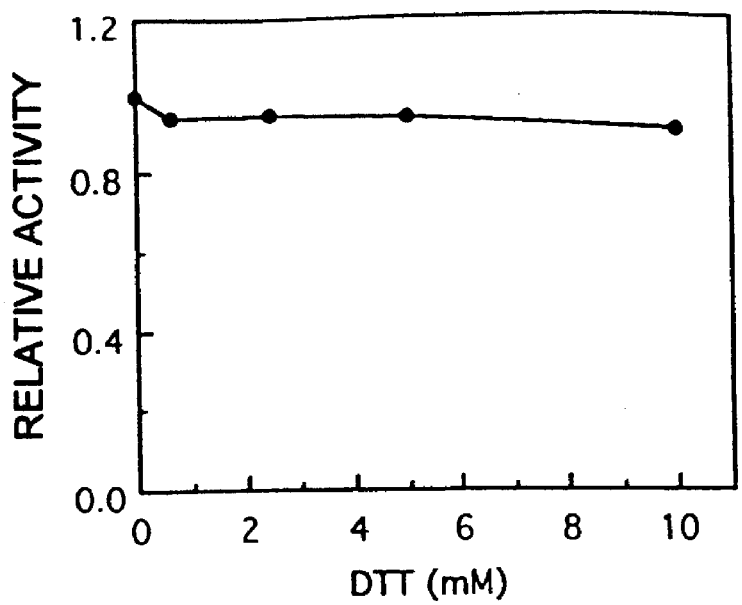
FIG. 11 shows a DTT concentration-enzyme activity curve demonstrating the influence of DTT on the enzyme of the present invention.

In order to investigate the influence of DTT on the activity of the enzyme of the present invention, DTT was added to a reaction solution at various concentrations to measure the enzyme activity (FIG. 11). DTT scarcely inhibited the activity up to 10 mM. This property is extremely different from that of heparan sulfate 6-sulfotransferase.

Figure 12:
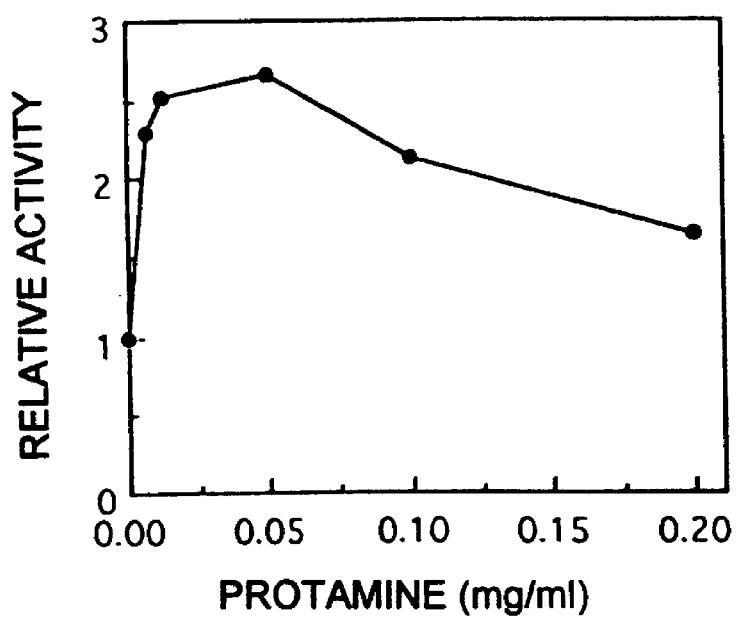
FIG. 12 shows a protamine concentration-enzyme activity curve demonstrating the influence of protamine on the enzyme of the present invention.

The influence of protamine on the enzyme activity of the enzyme of the present invention was investigated. A result is shown in FIG. 12. The activity of the heparan sulfate 2-sulfotransferase was remarkably increased by protamine in the same manner as chondroitin 4-sulfotransferase, chondroitin 6-sulfotransferase, and heparan sulfate 6-sulfotransferase.

As a result of investigation for the influence of 3',5'-ADP on the enzyme activity of the enzyme of the present invention, a strong inhibiting action was found in the same manner as other sulfotransferases.

(iv) Measurement of Michaelis Constant

Michaelis constant (Km) was determined for the enzyme of the present invention when CDSNS-heparin was used as a sulfate group acceptor and PAPS was used as a donor. PAPS (0.125 to 5 $\mu$M) was added to 50 $\mu$l of a reaction solution containing 0.19 unit of the enzyme of the present invention and 25 nmol of CDSNS-heparin as converted into an amount of hexosamine, and reacted at 37° C. for 20 minutes to measure initial velocities of the reaction. A Lineweaver-Burk plot was prepared, and Michaelis constant was calculated. As a result, Km of the enzyme of the present invention for PAPS was $2.0 \times 10^{-7}$M.

What is claimed is:

1. An isolated heparan sulfate 2-O-sulfotransferase having the following properties:

(i) action: sulfate group is transferred from a sulfate group donor selectively to the hydroxyl group at C-2 position of iduronic acid residue of a sulfate group acceptor, but not significantly to the hydroxyl group at C-6 position of glucosamine residue of the sulfate group acceptor;

(ii) substrate specificity: sulfate group is transferred to heparan sulfate, heparin or CDSNS-heparin, but sulfate group is not transferred to chondroitin, chondroitin sulfate, dermatan sulfate, and keratan sulfate;

(iii) optimum reaction pH: about 5 to 6.5;

(iv) optimum ionic strength: about 50 to 200 mM when sodium chloride is used; and (v) inhibition and activation: the activity of the enzyme is increased by protamine, the activity of the enzyme is inhibited by adenosine-3',5'-diphosphate, and the activity of the enzyme is substantially unaffected by dithiothreitol at 10 mM or less.

2. The heparan sulfate 2-O-sulfotransferase according to claim 1, wherein said sulfate group donor is 3'-phosphoadenosine 5'-phosphosulfate.

3. The heparan sulfate 2-O-sulfotransferase according to claim 1, which has a molecular weight of about 44 kDa or about 47 kDa as determined by sodium dodecyl sulfate polyacrylamide gel electrophoresis.

4. The heparan sulfate 2-O-sulfotransferase according to claim 1, which is a glycoprotein.

5. A method for producing heparan sulfate 2-O-sulfotransferase as defined in claim 1, comprising the steps of cultivating cells originating from an ovary of a Chinese hamster in a culture medium, and isolating the heparan sulfate 2-O-sulfotransferase from said medium.

6. The method for producing heparan sulfate 2-O-sulfotransferase according to claim 5, wherein said cells are CHO cells deposited as ATCC CCL61.

7. The method for producing heparan sulfate 2-O-sulfotransferase according to claim 6, wherein the isolating step comprises purification by adenosine-3',5'-diphosphate-affinity column chromatography.

8. The heparan sulfate 2-O-sulfotransferase according to claim 1, which has a Michaelis constant of about 0.20 $\mu$M for 3'-phosphoadenosine 5'-phosphosulfate when CDSNS-heparin is used as a sulfate group acceptor and 3'-phosphoadenosine 5'-phosphosulfate is used as a sulfate group donor.

9. A method for producing a 2-O-sulfated CDSNS-heparin or heparan sulfate comprising the steps of:

(a) incubating a reaction mixture comprising the heparan sulfate 2-O-sulfotransferase as defined in claim 1, 3'-phosphoadenosine 5'-phosphosulfate and CDSNS-heparin or heparan sulfate, to transfer sulfate group from the 3'-phosphoadenosine 5'-phosphosulfate to the hydroxyl group at C-2 position of iduronic acid residue of the CDSNS-heparin or heparan sulfate; and (b) isolating a 2-O-sulfated CDSNS-heparin or heparan sulfate from said reaction mixture.

* * * * *